United States Patent
Ellefson et al.

(10) Patent No.: US 7,399,484 B2
(45) Date of Patent: Jul. 15, 2008

(54) SYSTEM AND METHOD FOR PROVIDING THERAPY TO AN INDIVIDUAL

(75) Inventors: Kimberly L. Ellefson, Oshkosh, WI (US); James D. Milner, Appleton, WI (US); MeeWha Lee, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 763 days.

(21) Appl. No.: 10/880,975

(22) Filed: Jun. 30, 2004

(65) Prior Publication Data
US 2006/0002988 A1 Jan. 5, 2006

(51) Int. Cl.
*A61F 13/02* (2006.01)
*A61F 7/00* (2006.01)

(52) U.S. Cl. .................. 424/448; 604/291; 607/108

(58) Field of Classification Search ................. 424/448; 604/291, 304, 180; 607/108–111; 602/8, 602/9, 12, 47
See application file for complete search history.

(56) References Cited

U.S. PATENT DOCUMENTS

| | | | | |
|---|---|---|---|---|
| 3,918,446 | A | * | 11/1975 | Buttaravoli ................. 604/180 |
| 4,419,094 | A | * | 12/1983 | Patel ..................... 604/165.01 |
| 4,559,047 | A | * | 12/1985 | Kapralis et al. ............. 604/291 |
| 4,663,220 | A | | 5/1987 | Wisneski et al. |
| 5,226,992 | A | | 7/1993 | Morman |
| 5,476,490 | A | * | 12/1995 | Silver ......................... 607/108 |
| 5,685,859 | A | * | 11/1997 | Kornerup .................... 604/180 |
| 5,697,962 | A | * | 12/1997 | Brink et al. ................. 607/108 |
| 5,741,318 | A | * | 4/1998 | Ouellette et al. ............. 607/108 |
| 5,776,177 | A | * | 7/1998 | MacWhinnie et al. ......... 607/108 |
| 5,785,716 | A | * | 7/1998 | Bayron et al. ................ 607/108 |
| D417,007 | S | | 11/1999 | Davis et al. |
| D433,145 | S | | 10/2000 | Davis et al. |
| 6,206,902 | B1 | * | 3/2001 | Morikane ............... 606/204.15 |
| 6,500,200 | B1 | * | 12/2002 | Kushnir ....................... 607/104 |

(Continued)

FOREIGN PATENT DOCUMENTS

EP 0217032 A2 4/1987

(Continued)

OTHER PUBLICATIONS

"International Search Report for corresponding PCT Application PCT/US2005/017778", (Sep. 5, 2005), 3 pgs.

*Primary Examiner*—Sharon E. Kennedy
(74) *Attorney, Agent, or Firm*—Armstrong Teasdale LLP (57) ABSTRACT

The present invention relates to a patch and method for providing therapy to an individual. The patch and method provide a user or therapist with the flexibility to apply a patch to highly contoured areas on the individual's body. In some embodiments, the patch includes a body that applies therapy to the individual when the patch is placed on the individual. The patch further includes at least one cut in the body of the patch. In other example embodiments, the present invention relates to a method of providing therapy to an individual. The method includes selecting a patch that provides therapy to an individual. The patch includes a body and at least one cut in the body. The method further includes applying the patch to the individual where the cut in the body allows the patch to conform to the individual as the patch is applied to the individual.

23 Claims, 6 Drawing Sheets

U.S. PATENT DOCUMENTS

| | | | |
|---|---|---|---|
| 6,875,199 B2* | 4/2005 | Altman | 604/174 |
| 7,294,752 B1* | 11/2007 | Propp | 602/58 |
| 2003/0120194 A1* | 6/2003 | Stapf | 602/48 |
| 2004/0097588 A1 | 5/2004 | Daria et al. | |
| 2004/0097855 A1 | 5/2004 | Page et al. | |
| 2004/0097856 A1 | 5/2004 | Cipra et al. | |
| 2005/0125047 A1* | 6/2005 | Gammons | 607/104 |
| 2005/0192653 A1* | 9/2005 | Tsunakawa et al. | 607/109 |

FOREIGN PATENT DOCUMENTS

| | | |
|---|---|---|
| EP | 0934734 A1 | 8/1999 |
| WO | WO-98/05283 A1 | 2/1998 |
| WO | WO-03/057099 A1 | 7/2003 |

\* cited by examiner

SYSTEM AND METHOD FOR PROVIDING THERAPY TO AN INDIVIDUAL

FIELD

Some embodiments of this invention relate to a system and method for providing therapy to an individual, and in particular to a system and method that include placing a patch on an individual in order to provide therapy to the individual.

BACKGROUND

Applying therapy to various parts of a body is a recognized practice for curing or alleviating multiple kinds of physical problems. One example therapy involves cooling an area of a body by applying ice packs near the area of the body in an effort to reduce swelling, inflammation and/or muscle pain. Another example therapy applies heat to an area of a body using a heating pad to treat symptoms such as stiffness, muscle pain, cold hands and feet, lumbago, rheumatism and neuralgia (among others). Other therapies include applying an analgesic (for pain) or an antibiotic (for infection) to the area of the body.

One concern with using heating pads and ice bags to apply therapy is that they are difficult to attach to an area of a body because they need to be held in place by the injured person or someone assisting the injured person. Holding a heating pad or ice bag against an injured area of a body can cause patient discomfort because a relatively large force is typically required in order to keep the ice bag or heating pad in place.

Another method of cooling or heating an area of a body includes applying hot or cold patches against the area of the body. A patch is typically attached directly, or indirectly, to the area of the body using an adhesive. An analgesic and/or antibiotic may also be incorporated into such a patch in order to treat the area for pain and/or infection.

A typical cold patch generates cooling via an endothermic reaction that takes place within the cold patch. The cold patch usually includes a solute and a liquid that are both stored within a common enclosure. The liquid and solute are initially segregated from another within the enclosure and then mixed within the enclosure to form an endothermic solution that reduces the temperature of the cold patch.

A typical heat patch generates heat via an exothermic reaction that takes place within the heat patch. Heat patches that generate heat using an exothermic reaction usually include an enclosure and a heating composition which is stored within the enclosure. At least one section of the enclosure is air-permeable such that exposing the heating composition to air generates an exothermic reaction that increases the temperature of the heat patch.

One drawback with using patches to apply therapy is that they are typically made in certain sizes and shapes. Therefore, a particular patch may be suitable for applying therapy to some areas on an individual's body but not other areas. In addition, many conventional patches are unable to conform to highly contoured areas of an individual's body when the patches are applied to the individual.

There is a need for a patch and method that allow a user or therapist to conveniently provide therapy to an individual. The patch and method should allow a user or therapist to provide therapy to highly contoured areas of an individual's body.

SUMMARY OF THE INVENTION

The present invention relates to a patch and method for providing therapy to an individual. The patch and method provide a user or therapist with the flexibility to apply a patch to highly contoured areas on the individual's body.

In some example embodiments, the present invention relates to a patch for providing therapy to an individual. The patch includes a body that applies therapy to the individual when the patch is placed on the individual. The patch further includes at least one cut in the body of the patch. The body is separable at the cuts to give the patch more flexibility in the area of the cuts. In some embodiments, the body of the patch includes a perimeter and the cuts extend into the body from the perimeter of the body.

In other example embodiments, the present invention relates to a method of providing therapy to an individual. The method includes selecting a patch (e.g., a heat patch or a cooling patch) that provides therapy to an individual. The patch includes a body and at least one cut in the body. The method further includes applying the patch to the individual where the cut in the body allows the patch to conform to the individual as the patch is applied to the individual.

In still other example embodiments, the present invention relates to a method of fabricating a patch that provides therapy to an individual. The method includes forming a body that provides therapy to the individual when the patch is placed on the individual. The method further includes forming at least one cut in the body such that the body is separable at the cut to facilitate mounting the patch on the individual.

The purposes and features of the present invention will be set forth in the description that follows. Additional features of the invention will be realized and attained by the product and processes particularly pointed out in the written description and claims hereof, as well as from the appended drawings.

BRIEF DESCRIPTION OF THE DRAWINGS

The present invention will be more fully understood, and further features will become apparent, when reference is made to the following detailed description and the accompanying drawings. The drawings are merely representative and are not intended to limit the scope of the claims. Like parts depicted in the drawings are referred to by the same reference numerals.

DETAILED DESCRIPTION OF THE INVENTION

In the following detailed description, reference is made to the accompanying drawings, which show specific embodiments in which the invention may be practiced. These embodiments are described in sufficient detail to enable those skilled in the art to practice the invention. It is to be understood that other embodiments may be utilized and structural changes made, such that the following detailed description is not to be taken in a limiting sense.

Figure 1:
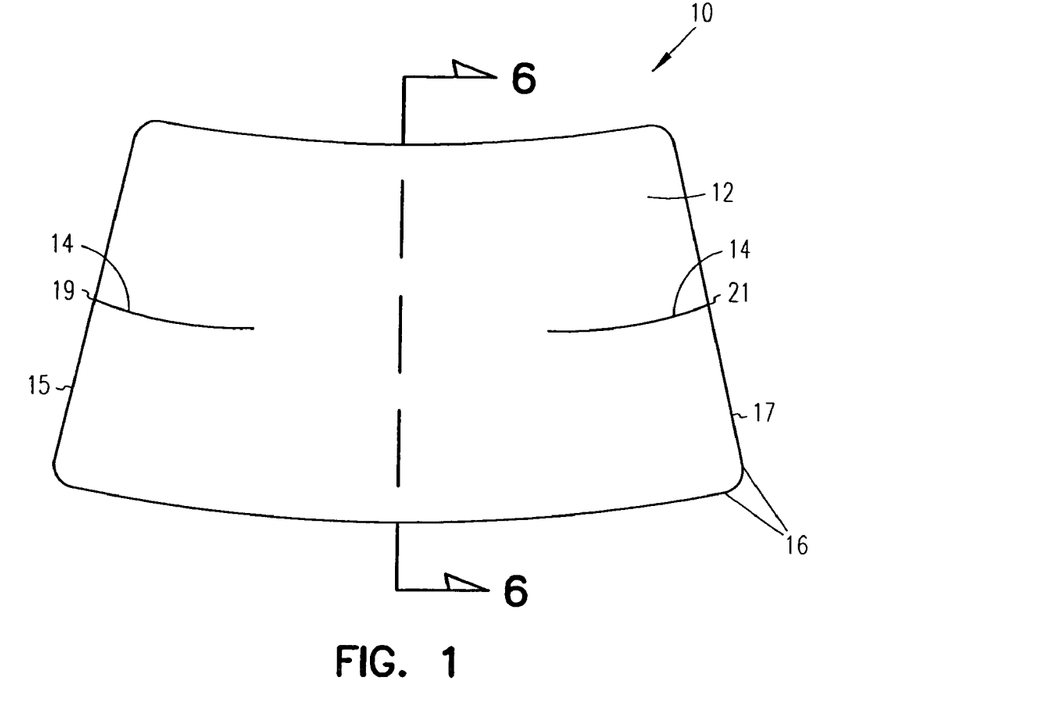
FIG. 1 is a plan view of an example patch for providing therapy to an individual.

FIG. 1 illustrates a patch 10 for providing therapy to an individual. The patch 10 includes a body 12 that applies therapy to the individual when the patch 10 is placed on the individual. The patch 10 further includes at least one cut 14 in the body 12.

Figure 2:
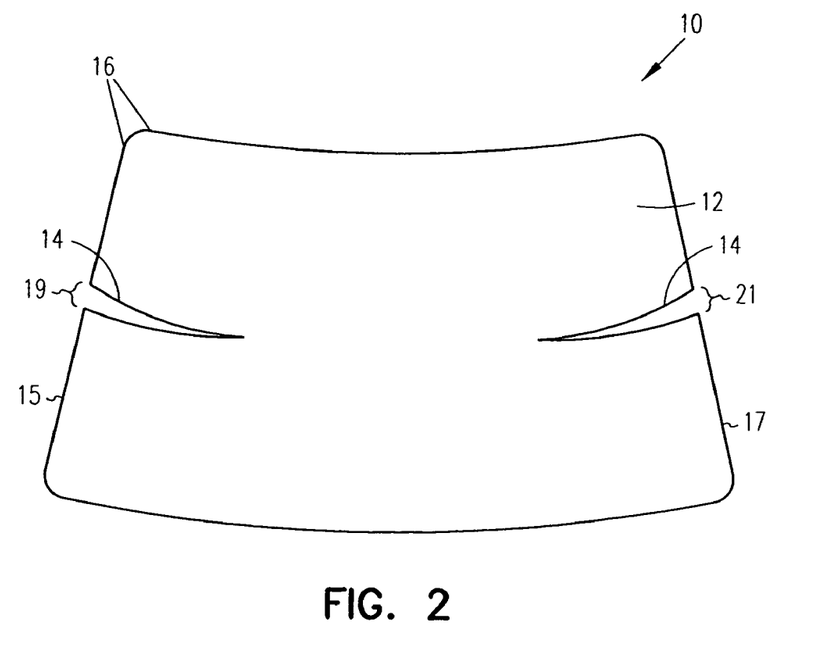
FIG. 2 is a plan view of the patch shown in FIG. 1 with cuts in the body of the patch separated.

As shown in FIG. 2, the body 12 of the patch 10 is separable at the cuts 14. In the example embodiment illustrated in FIGS. 1 and 2, the body 12 includes a perimeter 16 and the cuts 14 extend into the body 12 from the perimeter 16 of the body 12.

Figure 3:
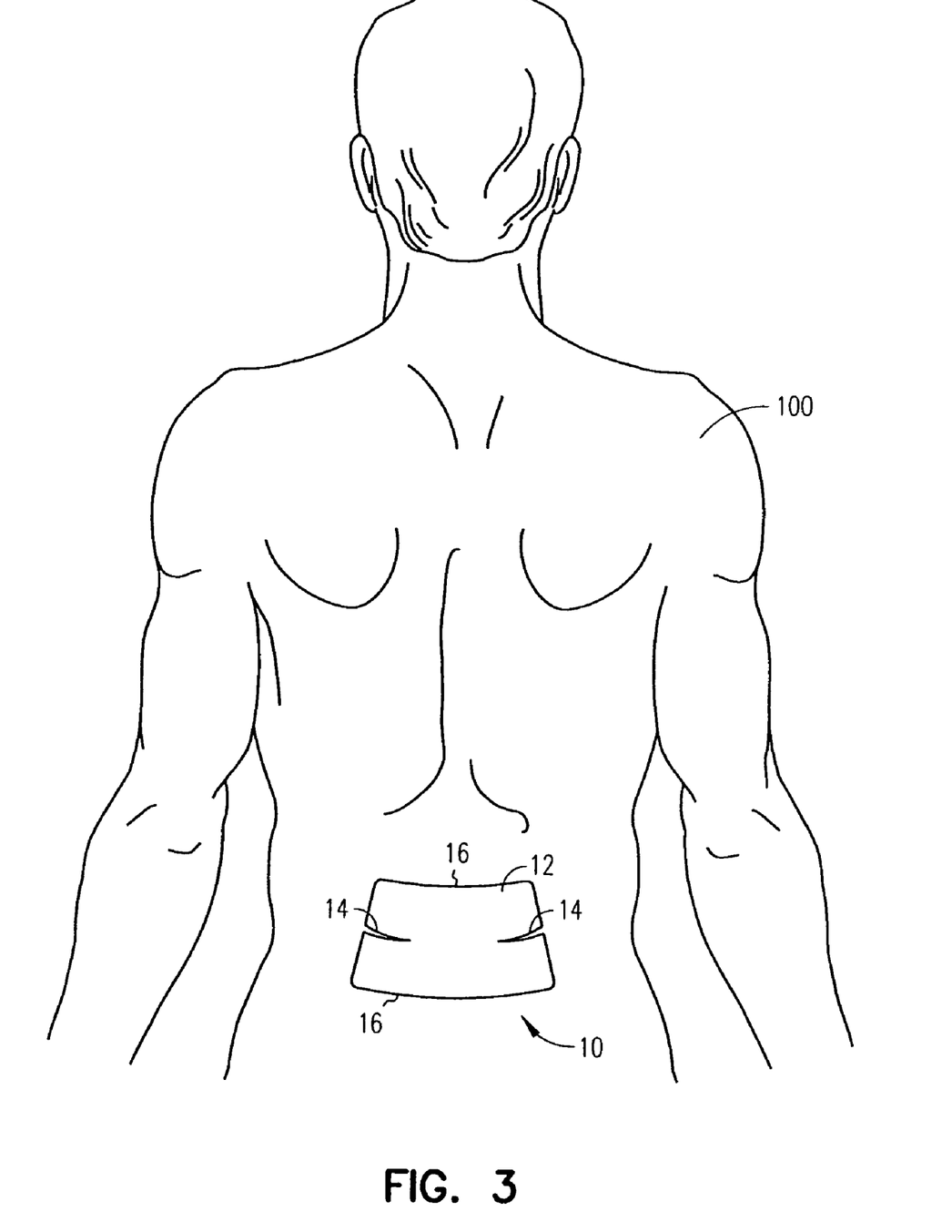
FIG. 3 is a plan view illustrating the patch shown in FIGS. 1 and 2 mounted onto an individual.

FIG. 3 illustrates that when patch 10 is applied to an individual 100, the cuts 14 may give the patch 10 more flexibility in the area of the cuts 14. The increased flexibility of the patch 10 at the cuts 14 may allow the patch 10 to fit more readily onto a highly contoured area of the individual 100.

Referring again to FIGS. 1 and 2, the body 12 may be comma-shaped and include a first end 15 and a second end 17. A first cut 14 may extend into the body 12 from a midsection 19 of the first end 15 and a second cut 14 may extend into the body 12 from a midsection 21 of the second end 17.

Although body 12 is shown as comma-shaped in FIGS. 1 and 2, it should be noted that body 12 may be other shapes and/or sizes. The proper size and shape of the patch 10 will depend on the application where the patch 10 is used. In some forms, the patch 10 may be long enough to fit around the arms, legs, head or torso of an individual's body.

As used herein, patch refers to any type of patch, pack, bag or pouch that may be used to apply therapy to a body. In addition, patch 10 may be capable of being attached directly, or indirectly, to an individual.

Figure 4:
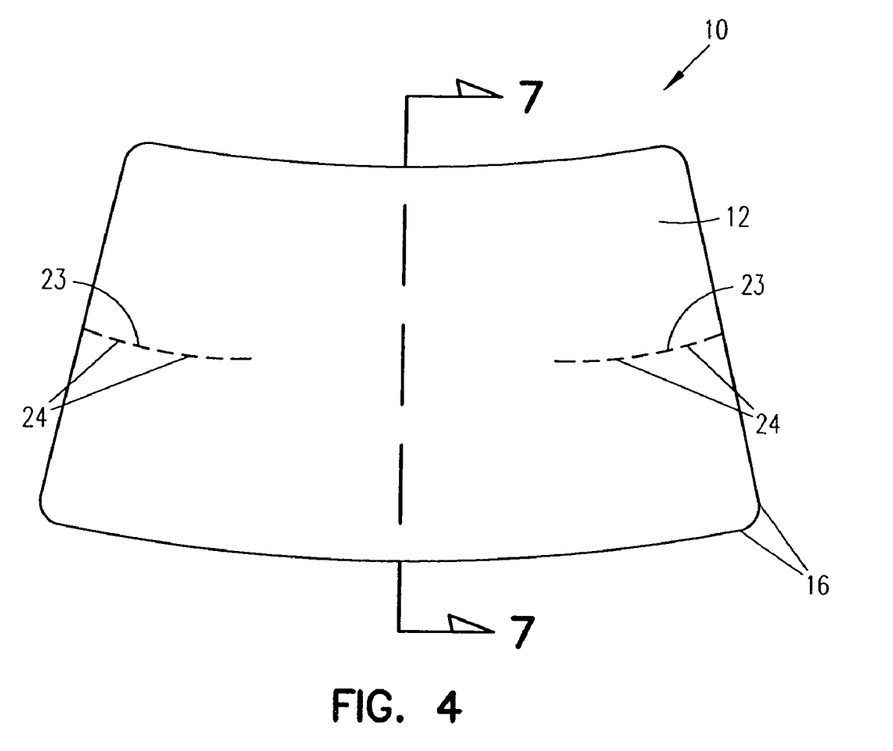
FIG. 4 is a plan view of another example embodiment of the patch for providing therapy to an individual.
Figure 5:
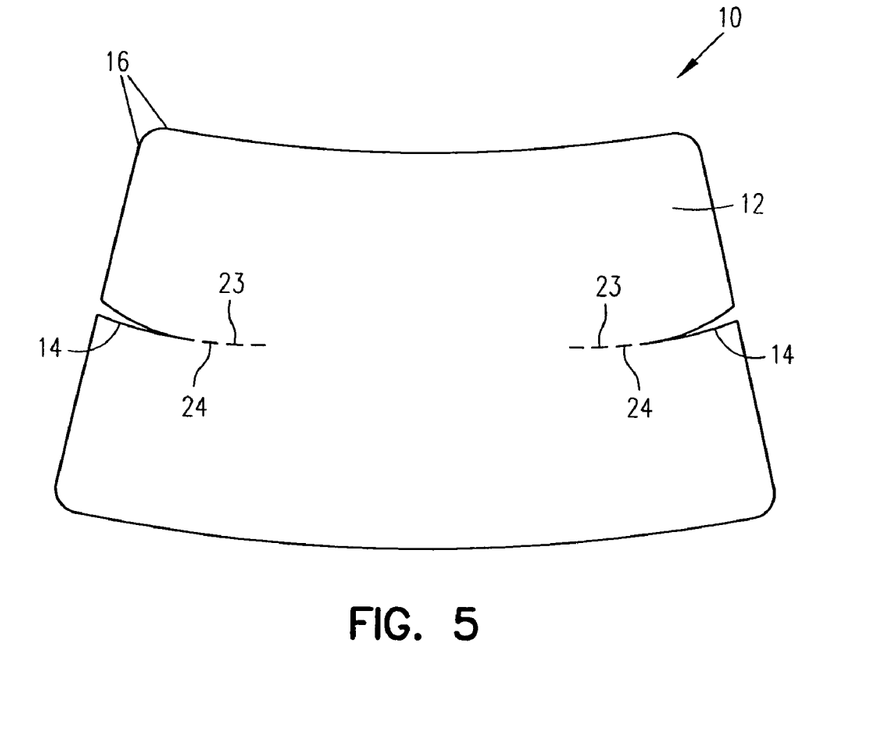
FIG. 5 is a plan view of the patch shown in FIG. 4 with perforations in the body of the patch torn to form cuts in the body of the patch.

As shown in FIGS. 4-5, patch 10 may include perforated sections 23 (FIG. 4) that are partially, or completely torn to form cuts 14 (FIG. 5). In some embodiments, the perforated sections 23 are formed of slits 24. Although slits 24 are shown in FIG. 4, it should be noted that other types of perforations, such as holes and indentations (among others) may be included in body 12.

The slits 24 may be formed in the perforated sections 23 by slicing portions of the body 12. The ratio of the material that is sliced to the material that is not sliced within the perforated sections 23 determines the size of the slits 24. As the total size of the slits 24 in each perforated section 23 increases, it becomes easier to form cuts 14 by tearing perforated sections 23.

In other embodiments, the cuts 14 may be formed by slicing the body 12 of the patch 10. It should be noted that the cuts 14 may be linear, curved, comma-shaped or any other shape that facilitates mounting the patch 10 onto an individual 100.

Figure 6:
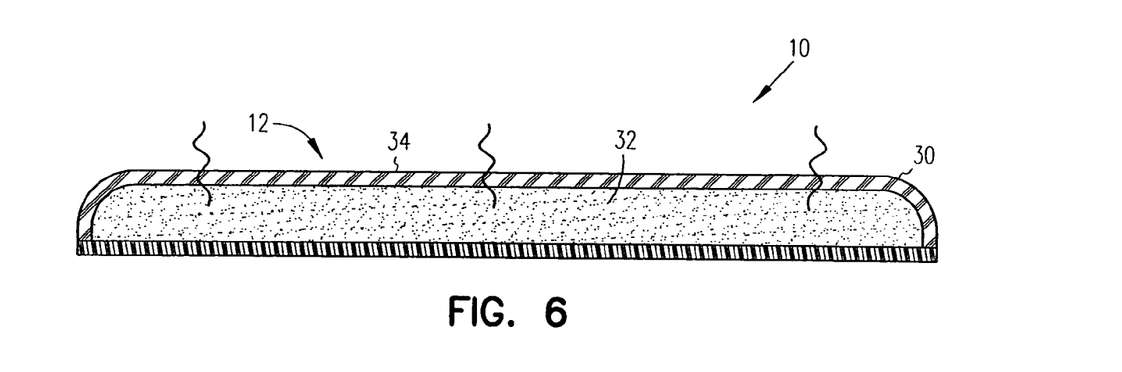
FIG. 6 is a section view of the patch shown in FIG. 1 taken along line 6-6 illustrating an example embodiment where the patch is a heat patch.

FIG. 6 illustrates an example embodiment where the patch 10 is a heat patch that may be used to apply heat therapy to individual 100. In some forms, the body 12 of the heat patch 10 may include an enclosure 30 and a heating composition 32 that is sealed inside the enclosure 30. The heating composition 32 may be capable of generating heat when a gas, such as oxygen contained in ambient air, is received through a gas-permeable section 34 of the enclosure 30.

When the patch 10 is a heat patch, it may be stored in a hermetic environment (e.g., a sealed bag) such that the heating composition remains inactive until the heat patch is removed from the hermetic environment. Once the patch 10 is removed from the hermetic environment, the heating composition 32 within the enclosure 30 is exposed to air such that an exothermic reaction takes place within the body 12 of the heat patch 10. The exothermic reaction generates heat within the patch 10 to increase the temperature of the patch 10.

Any conventional heating composition may be used to induce an exothermic reaction within patch 10. Some example heating compositions include iron powder as the main active ingredient.

Figure 7:
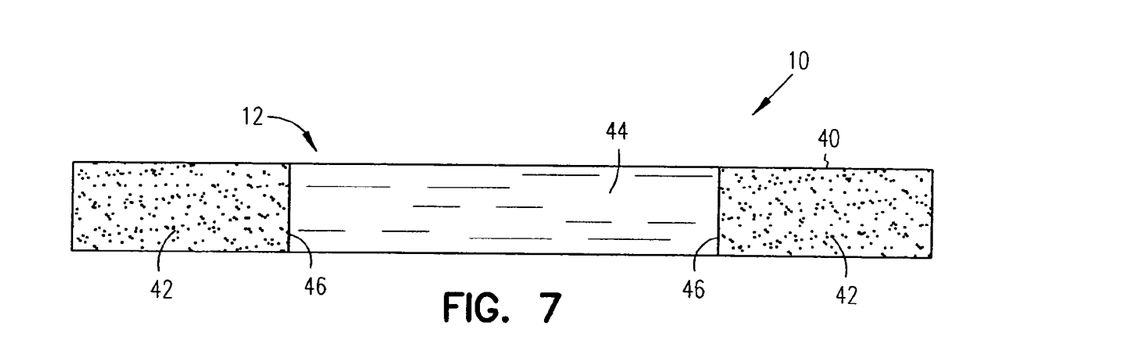
FIG. 7 is a section view of the patch shown in FIG. 4 taken along line 7-7 illustrating an example embodiment of a cooling patch that includes an endothermic solute and a liquid which are segregated inside an enclosure by a membrane.
Figure 8:
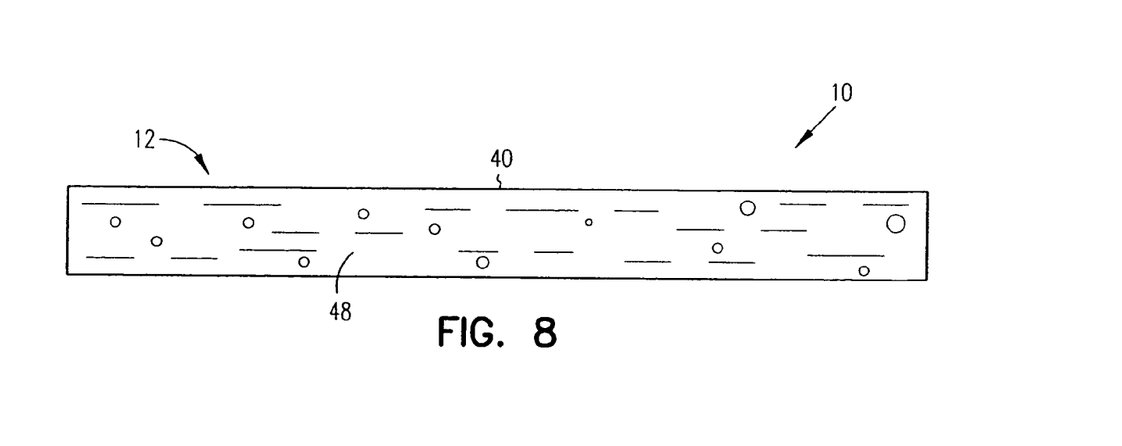
FIG. 8 is a section view similar to FIG. 7 where the membrane within the enclosure is ruptured to mix the endothermic solute with the liquid to form an endothermic solution inside the enclosure.

FIGS. 7 and 8 illustrate another example embodiment where the patch 10 is a cooling patch that may be used to apply cooling therapy to individual 100. In some forms, the body 12 of the patch 10 may include an enclosure 40 that has a solute 42 and a liquid 44 sealed inside the enclosure 40. The solute 42 and the liquid 44 are initially segregated within the enclosure 40 by a membrane 46 (FIG. 7). Rupturing the membrane 46 within the enclosure 40 (e.g., by applying pressure to the enclosure 40) mixes the liquid 44 with the solute 42 to produce an endothermic solution 48 within the enclosure 40 (FIG. 8).

Any conventional endothermic solute may be used to induce an endothermic reaction within the cold patches. One example endothermic solute includes ammonium nitrate.

It should be noted that in any of the patches 10 shown, described and/or referenced herein, one or more of the patches may include a medication, such as a transdermal and/or topical medication that is applied to the individual 100. Some example medications include topical analgesics and/or antibiotics.

In addition, any of the patches 10 may be treated with a variety of therapeutic additives, such as herbs, vitamins and/or botanicals. Some example botanicals include lavender, chamomile, moisturizers, lipids, essential oils and fragrances. Another example therapeutic additive may include magnetic elements, such as particles chips, and/or disks. The therapeutic additives could be inside the patches or sprayed directly on the patches.

It should be noted that any of the patches 10 described herein may also include non-steroidal anti-inflammatory drugs. Some example non-steroidal anti-inflammatory agents include aspirin, ibuprophen, ketoprophen and naproxen sodium (among others). In some forms, the non-steroidal anti-inflammatory agents may be drugs that are available by prescription only.

The patch 10 may also be applied to an affected skin area to deliver treatment from various skin ailments. Some example ailments include irritation due to sun burns, heat burns, insect bites, athletes foot, dry skin, or other chronic skin conditions.

It should be noted that any combination of the therapies described herein may be part of patch 10. As an example, patch 10 may be a heat patch that also includes a transdermal analgesic.

Figure 9:
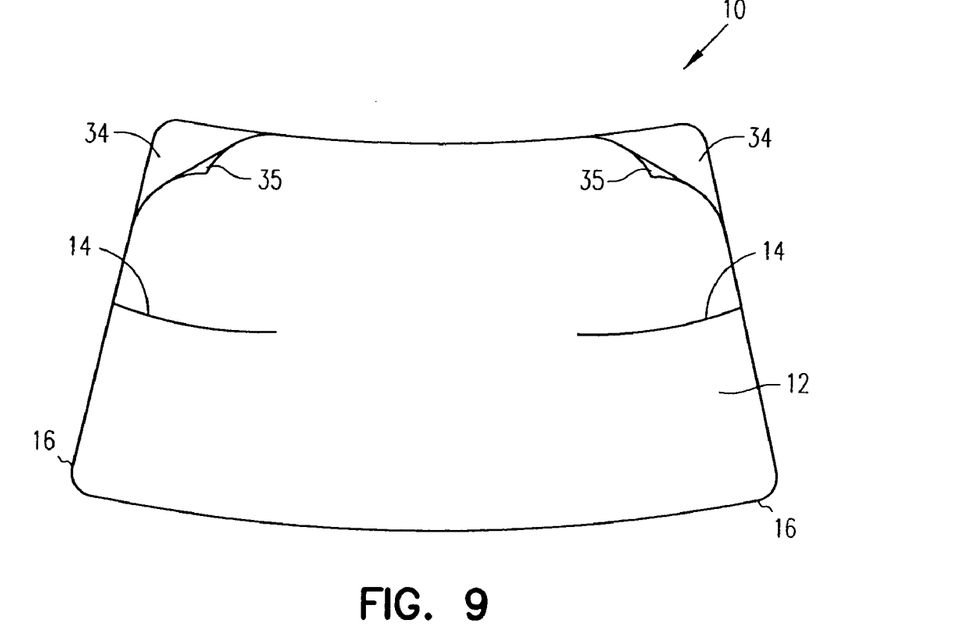
FIG. 9 is a plan view illustrating an example opposing side of the patch that is illustrated in FIGS. 1-2.

FIG. 9 shows an opposing side of the patch 10 that is illustrated in FIGS. 1-2. In the illustrated example embodiment, patch 10 includes an adhesive 34 that is mounted on the patch 10 in order to secure the patch 10 to individual 100. The patch 10 may further include a releasable cover 35 that is mounted on the adhesive 34 to protect the adhesive 34. When the patch 10 is attached to the individual 100, the releasable cover 35 may be removed to expose the adhesive 34.

In some embodiments, the adhesive 34 may include a styrene-isoprene-styrene copolymer. As examples, the adhesive may be a hot melt, silicone or a hydrogel, although any conventional adhesive may be used. In addition, the releasable cover 35 may be a polyethylene film, silicone coated paper or any other material that can be separated from the adhesive 34.

Figure 10:
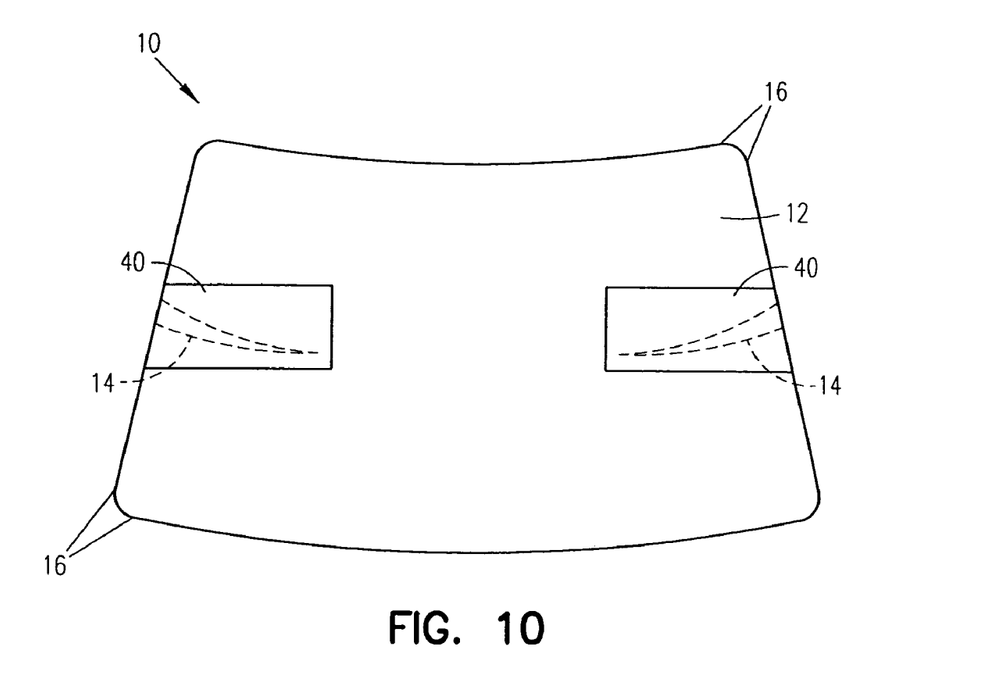
FIGS. 10 and 11 are plan views showing additional example embodiments for the opposing side of patch with the cuts in the patch separated for sake of illustration.
Figure 11:
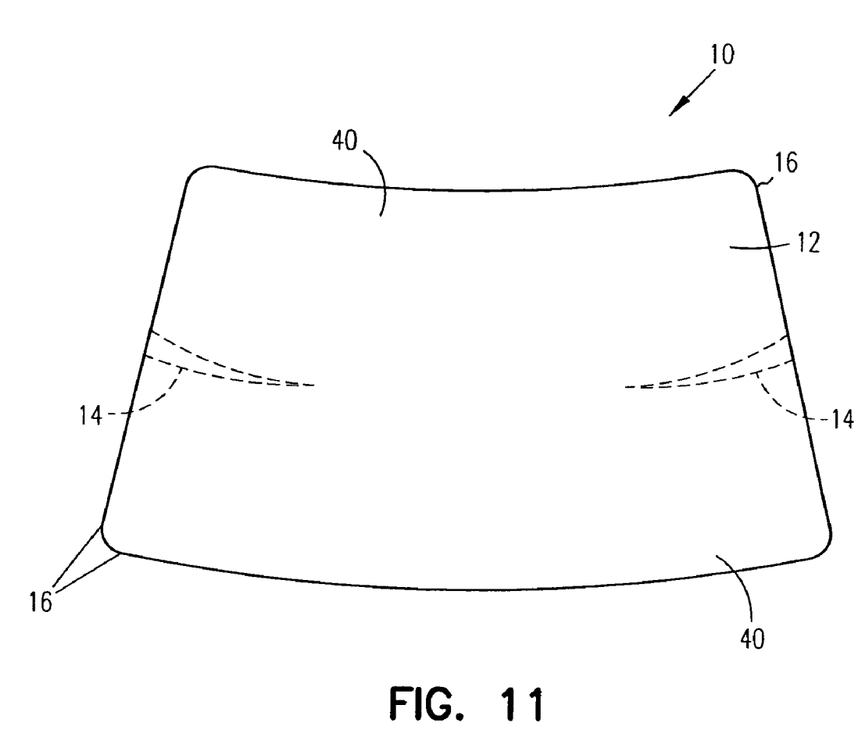

FIGS. 10 and 11 show additional example embodiments for the opposing side of patch 10 with the cuts 14 in the patch 10 separated for sake of illustration. In the example embodiments illustrated in FIGS. 10 and 11, patch 10 includes at least one additional layer 40 that is attached to the body 12 over one or more of the cuts 14 in the body 12. It should be noted that the layer 40 may cover only those portions of the body 12 where the cuts 14 are located (FIG. 10), or may cover one entire side of the body 12 (FIG. 11).

The layer(s) 40 may be more elastic or extensible than the body 12 to provide some resiliency to the patch 10 at the cuts 14 in the body 12. An elastic or extensible material is capable of elongation in at least one direction. A material that is elastic is capable of recovery or retraction upon release of a stretching force while a material that is extensible has limited recovery upon release of a stretching force. Some example materials for the layer(s) 40 include elastic or extensible filaments, films, foams, netting, webs, or laminates of two or more materials (among others).

Example elastic materials include spandex or natural rubber. In addition, laminates could include stretch-bonded-laminates or neck-bonded-laminates. The methods of making such materials are well known to those skilled in the art and are described in U.S. Pat. No. 4,663,220 to Wisneski et al., U.S. Pat. No. 5,226,992 to Morman, and European Patent Application No. EP 0217032 to Taylor et al.

A method of providing therapy to an individual 100 is described herein with reference to FIGS. 1-11. The method includes selecting a patch 10 (e.g., a heat patch or a cooling patch) that provides therapy to an individual 100. The patch 10 includes a body 12 and at least one cut 14 in the body 12. The method further includes applying the patch 10 to the individual 100 where the cut 14 in the body 12 allows the patch 10 to conform to the individual 100 (FIG. 3) as the patch 10 is applied to the individual 100.

FIGS. 4 and 5 show that some embodiments of the method may further include tearing perforated sections 23 of the body 12 to form cuts 14 in the body 12. In addition, FIG. 3 shows that patch 10 may be applied directly to skin on the individual 100, although in other embodiments patch 10 may be applied onto clothing or a bandage that covers the individual 100.

In some embodiments, applying the patch 10 to the individual 100 may include releasing a cover 35 that protects an adhesive 34 on the patch 10 and adhering the patch 10 to the individual 100 using the adhesive 34 (FIG. 9). The patch 10 may also be held against the individual 100 using an adhesive bandage, elastic bandage, tape, wrap and/or elastic wrap (among other items).

It should be noted that patch 10 may include any number of cuts 14 such that applying the patch 10 to the individual 100 includes separating the plurality of cuts 14 in the body 12 to conform the patch 10 to the individual 100. The proper number, size, type and shape of the cuts 14 will depend on the application where patch 10 is used.

A method of fabricating a patch 10 that provides therapy to an individual 100 is described herein with reference to FIGS. 1-11. The method includes forming a body 12 that provides therapy to the individual 100 when the patch 10 is placed on the individual 100. The method further includes forming at least one cut 14 in the body 12 such that the body 12 is separable at the cut 14 to facilitate mounting the patch 10 on the individual 100 (FIG. 3).

In some embodiments, forming a body 12 may include forming perforated sections 23 in the body 12 such that the cuts 14 are formed by tearing the perforated sections 23 (see, e.g., FIGS. 4 and 5). In other embodiments, forming the cuts 14 in the body 12 may include slicing the body 12 to form the cuts 14. It should be noted that the cuts 14 may be formed in the body 12 sequentially or simultaneously. The increased flexibility of the patch 10 at the cuts 14 may allow the patch 10 to fit more readily onto a highly contoured area of the individual 100.

In some sample embodiments, forming a body 12 may include forming a body 12 that includes an enclosure and a material inside the enclosure (see, e.g., enclosure 30 in FIG. 6 and enclosure 40 in FIGS. 7 and 8). As an example, the method may include placing an exothermic material inside the enclosure (FIG. 6).

As shown in FIGS. 10 and 11, the method may further include placing one or more layers 40 on the body 12 of the patch 10 over the cuts 14 in the body 12 (one layer 40 is shown in FIGS. 10 and 11). The layer 40 may be more elastic than the body 12 such that the layer 40 provides some resiliency to the patch 10 at the cuts 14 in the body 12.

The operations discussed above with respect to the described methods may be performed in a different order from those described herein. In addition, FIGS. 1-11 are representational and are not necessarily drawn to scale. Certain proportions thereof may be exaggerated, while others may be minimized.

While the invention has been described in detail with respect to the specific aspects thereof, it will be appreciated that those skilled in the art, upon attaining an understanding of the foregoing, may readily conceive of alterations to, variations of, and equivalents to these aspects which fall within the spirit and scope of the present invention, which should be assessed accordingly to that of the appended claims.

We claim:

1. A patch for providing therapy to an individual, the patch comprising:
   a body that applies therapy to the individual when the patch is placed on the individual, the body including an enclosure filled with a material;
   a cut in the body, the body being separable at the cut to facilitate mounting the patch on the individual; and
   a layer that is attached to the body over the cut.

2. The patch of claim 1 wherein the enclosure includes a gas-permeable section and the material is an exothermic material that reacts with air which is received though the gas-permeable section of the enclosure.

3. The patch of claim 1 wherein the enclosure is filled with an endothermic material and a liquid that can be mixed together to form an endothermic solute.

4. patch of claim 1 wherein the body includes an antibiotic.

5. patch of claim 1 wherein the body includes an analgesic.

6. The patch of claim 1 wherein the body includes an anti-inflammatory agent.

7. The patch of claim 1 wherein the body includes a perimeter and the cut extends into the body from the perimeter of the body.

8. The patch of claim 1 wherein the cut is linear.

9. The patch of claim 1 wherein the body is comma-shaped.

10. The patch of claim 9 wherein the body includes a first end and a second end such that a first cut extends into the body from a midsection of the first end and a second cut extends into the body from a midsection of the second end.

11. The patch of claim 10 wherein the first cut is comma-shaped and the second cut is comma-shaped.

12. The patch of claim 1 further comprising an adhesive that is mounted on the body to secure the patch on the individual.

13. The patch of claim 1 wherein the layer is more elastic than the body.

14. The patch of claim 1 wherein the layer covers one side of the body.

15. A method of providing therapy to an individual, the method comprising:
   selecting a patch that provides therapy, the patch including a body and a cut in the body such that a layer is attached to the body over the cut, the body being at least partially formed of an enclosure that is filled with a material; and
   applying the patch to the individual, the cut in the body allowing the body of the patch to conform to the individual.

16. The method of claim 15 wherein applying the patch includes applying the patch to skin on the individual.

17. method of claim 15 wherein applying the patch includes adhering the patch to the individual using an adhesive.

18. The method of claim 15 wherein the body of the patch includes a plurality of cuts such that applying the patch includes separating the plurality of cuts in the body to conform the patch to the individual.

19. The method of claim 15 wherein applying the patch includes applying a heat patch to the individual.

20. A method of fabricating a patch that provides therapy to an individual, the method comprising:
   forming a body that includes an enclosure and a material inside the enclosure such that the body provides therapy to the individual when the patch is placed on the individual; forming a cut in the body such that the body is separable at the cut to facilitate mounting the patch on the individual; and
   placing a layer on the body of the patch over the cut in the body to support the patch at the cut in the body.

21. The method of claim 20 wherein forming a cut in the body includes slicing the body to form the cut.

22. The method of claim 20 further comprising forming a plurality of cuts in the body such that the body is separable at each of the cuts to facilitate mounting the patch on the individual, and wherein placing a layer on the body of the patch over the cut in the body to support the patch at the cut in the body includes placing a layer on the body of the patch over each cut in the body.

23. The method of claim 20 wherein forming a body that includes an enclosure and a material inside the enclosure includes placing an exothermic material inside the enclosure.

* * * * *

UNITED STATES PATENT AND TRADEMARK OFFICE
CERTIFICATE OF CORRECTION

PATENT NO.         : 7,399,484 B2
APPLICATION NO. : 10/880975
DATED              : July 15, 2008
INVENTOR(S)        : Ellefson et al.

It is certified that error appears in the above-identified patent and that said Letters Patent is hereby corrected as shown below:

In Claim 2, column 6, line 51, delete "though" and insert therefor -- through --.

In Claim 4, column 6, line 56, before "patch" insert therefor -- The --.

In Claim 5, column 6, line 57, before "patch" insert therefor -- The --.

In Claim 17, column 7, line 23, before "method" insert therefor -- The --.

Signed and Sealed this

Twenty-sixth Day of May, 2009

JOHN DOLL
*Acting Director of the United States Patent and Trademark Office*